United States Patent [19]

Wagner et al.

[11] Patent Number: 4,983,731
[45] Date of Patent: Jan. 8, 1991

[54] SEPARATION AND PURIFICATION OF SUGAR ESTERS

[75] Inventors: Frederick W. Wagner, Walton; Maria A. Dean, Lincoln; Rebecca S. de la Motte, Lincoln; Virginia H. Stryker, Lincoln, all of Nebr.

[73] Assignee: Nebraska Department of Economic Development, Nebr.

[21] Appl. No.: 325,199

[22] Filed: Mar. 17, 1989

[51] Int. Cl.$^5$ .................. C07H 1/00; C07H 13/02
[52] U.S. Cl. .................. 536/127; 536/119; 536/115; 536/18.6; 536/120
[58] Field of Search .............. 536/127, 119, 115, 18.6, 536/120

[56] References Cited

U.S. PATENT DOCUMENTS

| | | | |
|---|---|---|---|
| 2,893,990 | 7/1959 | Hass et al. | 536/119 |
| 2,948,716 | 8/1960 | Davis | 536/119 |
| 3,558,597 | 1/1971 | von Brachel et al. | 536/119 |
| 3,644,333 | 2/1972 | Osipow et al. | 536/119 |
| 4,104,464 | 8/1978 | James | 536/115 |

Primary Examiner—Ronald W. Griffin
Assistant Examiner—Everett White
Attorney, Agent, or Firm—Merchant, Gould, Smith, Edell, Welter & Schmidt

[57] ABSTRACT

The process uses two steps to separate the sugar ester from the crude sugar ester reaction product. The first step entails forming a precipitate of sugar ester from a mixture of alcohol, water and crude sugar ester reaction product. In a second subsequent step, the recovered sugar ester precipitate is washed with an organic solvent.

16 Claims, 2 Drawing Sheets

SEPARATION AND PURIFICATION OF SUGAR ESTERS

The present invention relates to the separation and purification of sugar esters of fatty acids and, more particularly, the separation and purification of sugar esters of fatty acids from a crude sugar ester reaction product obtained from transesterification of a fatty acyl ester with sugar. The present invention is especially useful for separation and purification of sucrose esters.

Sugar esters of fatty acids, hereinafter referred to as sugar esters, are known for their ability to act as surfactants and non-ionic emulsifiers. Sugar esters are especially useful in the food, pharmaceutical and cosmetic industries because they are considered non-toxic, edible and able to degrade into naturally occurring substances.

One well-known and highly commercial process used to make sugar esters is a transesterification process between a fatty acyl ester and sugar in the presence of a base catalyst in an anhydrous solvent such as N,N-dimethylformamide (DMF) or dimethylsulfoxide (DMSO). Such a process, is taught in U.S. Pat. No. 2,893,990 (hereinafter the '990 patent) issued July 7, 1959. Typically, the synthetic process of the '990 patent results in a crude sugar ester reaction product which contains the sugar ester, the base catalyst, the anhydrous solvent as well as unreacted sugar, unreacted fatty acyl ester and decomposed reagents.

Another well-known process for making sugar esters and especially sucrose esters is the so-called "transparent emulsion" process. In the transparent emulsion process, a sugar such as sucrose is combined with fatty acyl ester and an emulsifying agent to form a transparent emulsion. The transparent emulsion is subjected to alkaline condition at about 60° to 200° C. to convert the sugar to a sugar ester of the fatty acid. The reaction is carried out in a liquid medium such as water. Such a process is taught in U.S. Pat. No. 3,644,333 hereinafter the '333 issued Feb. 22, 1972.

The resulting crude sugar ester reaction product from the transparent emulsion process is visually a dark solid mass composed of sugar ester, unreacted and decomposed sugar, catalysts as well as other unreacted and decomposed starting materials.

Typically, sugars used for making sugar esters include sucrose, raffinose and glucose with sucrose being preferred. Typical fatty acids used in such synthesis processes include lauric, myristic, palmitic and stearic acid and fatty acyl esters such as methyl palmitate, methyl sterate and ethyl laurate are conventionally used in the transesterification reaction.

Previous purification methods for separating and purifying the sugar ester from the crude sugar ester reaction product have relied upon a variety of methods such as solvent distillation in vacuo (U.S. Pat. Nos. 2,948,716 and 3,054,789), extraction with organic solvents (U.S. Pat. No. 3,045,789), pH adjustment, and addition of mineral acids or metal salts (U.S. Pat. Nos. 3,748,324 and 4,104,464). These methods are complicated and involve a substantial cost to the user.

SUMMARY OF THE INVENTION

A method for purification and separation of sugar esters, especially sucrose esters, has now been discovered which is relatively uncomplicated and allows for separation and purification of sugar esters from a crude sugar ester reaction product obtained from both a transparent emulsion synthesis process and a synthesis process that employs an anhydrous solvent such as DMF or DMSO. With respect to the crude sugar ester reaction product obtained from a synthesis process that employs an anhydrous solvent like the process taught in the '990 patent, it has been discovered that the separation and purification process of the present invention does not require distillation of the reaction solvent, pH adjustment or the addition of acids or salts. With respect to the crude sugar ester reaction product obtained from the transparent emulsion process, it has been found that by employing the separation and purification process of the present invention that pH adjustment or addition of acids or salts are not needed. Additionally, the method of the present invention removes coloring and odor causing substances which result from decomposed reagents.

In one aspect, the present invention is a method for separating and purifying sugar esters from a transesterification reaction mixture in solvent, comprising the steps of:
(a) forming a mixture of crude sugar ester reaction product reaction solvent, water and an aliphatic alcohol having from 1 to 4 carbon atoms to cause precipitation of the sugar ester;
(b) recovering a precipitated sugar ester from said mixture;
(c) washing said precipitated sugar ester with a volatile organic solvent; and
(d) recovering an organic solvent washed sugar ester.

The preferred alcohols are methanol, ethanol, propanol, isopropanol, normal butanol, isobutanol and secondary butanol.

The preferred volatile organic solvents are ketones having 3 to 6 carbon atoms and ethers having 4 to 8 carbon atoms. Such volatile organic solvents are diethyl ether, dipropyl ether, methylpropyl ether, methyl ketone, methyl ethyl ketone and methyl isobutyl ketone.

In another aspect, when the crude sugar ester reaction product is obtained from a transparent emulsion process such as the one taught in the '333 patent, the step to precipitate the crude sugar ester product with water and alcohol is accomplished in a two step mixing process. First, the crude sugar ester reaction product is mixed with the aliphatic alcohol at a temperature of about 40° C. and above to form a solid phase and a liquid phase. The liquid phase contains crude sugar ester. The second mixing step entails mixing the liquid phase which results from mixing the crude sugar ester reaction product with the alcohol, with water at a temperature about 40° C. and above. A crude sugar ester precipitate is recovered by allowing the mixture of crude sugar ester, water and alcohol to stand without agitation and allowing the mixture to cool to below about 30° C. All the sugar ester precipitates from the liquid mix. As soon as the water is mixed with the liquid phase of crude sugar ester and alcohol, precipitate starts to form. Cooling the solution forces the remainder of the sugar ester to precipitate out of solution.

When the crude sugar ester reaction product is obtained from an anhydrous solvent synthesis process such as the one taught in the '990 patent, it is preferable to subject the precipitated sugar ester to a wash of alcohol and water prior to the organic solvent wash. The alcohol water wash step entails washing the precipitated sugar ester with an alcohol-water mix comprising water and an aliphatic alcohol having 1 to 4 carbon atoms. Suitable alcohols for use in the alcohol water wash include methanol, ethanol, propanol, isopropanol, normal butanol, isobutanol and secondary butanol.

BRIEF DESCRIPTION OF THE DRAWINGS

These and other aspects of the present invention may be more fully understood by reference to the accompanying drawings wherein.

DETAILED DESCRIPTION OF THE INVENTION

Embodiments of the purification method of the invention can be readily understood by a specific application of the method to a crude reaction material from (a) a transesterification process and (b) a transparent emulsion process.

Figure 1:
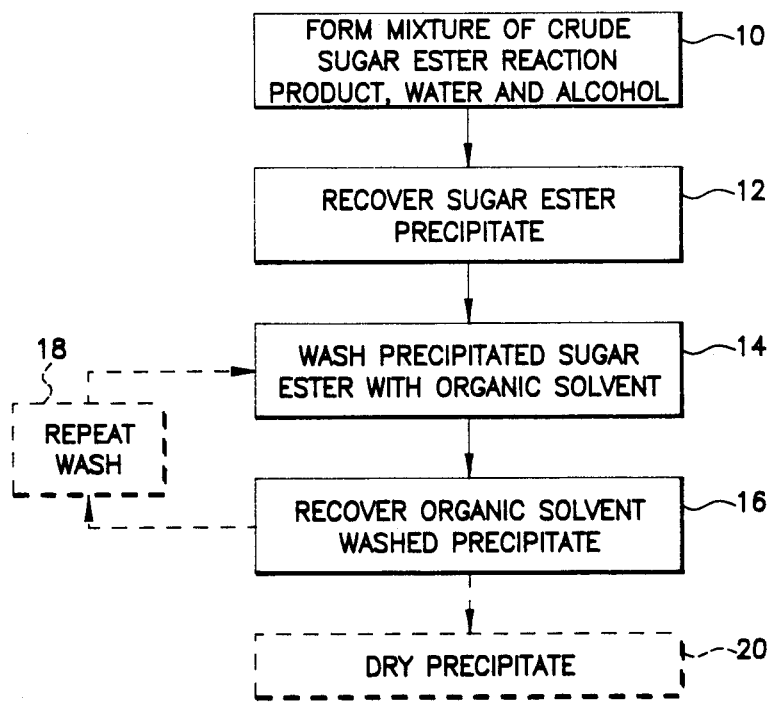
FIG. 1 illustrates the steps employed in the present invention to purify a sugar ester from a transparent emulsion process.

As illustrated in FIG. 1, a reaction mixture containing other reactants, sugar ester products and solvents in a transesterification process, water and aliphatic alcohol having from 1 to 4 carbons is formed (See step 10 of FIG. 1). Such a mixture is formed in a conventional manner by mixing all the components together using conventional mixing apparatus such as a beaker with a magnetic stirrer or a vat with an impeller. The mixing is conducted at ambient temperature and pressure. The water is obtained from any conventional source, deionized water is preferred. Suitable alcohols include methanol, ethanol, propanol, isopropanol, normal butanol, isobutanol, and secondary butanol; ethanol is preferred. Mixing is conducted until the crude sugar ester reaction product, water and alcohol are thoroughly mixed, all solid suspended or dissolved in solution. The volume of water and alcohol combined must be enough to suspend or dissolve the solid crude sugar ester reaction product. Good results have been obtained using a volume:volume ratio of water and alcohol:crude sugar ester reaction product of about 1:1.

Next, a precipitate of sugar ester is recovered from the mixture (see the step 12 of FIG. 1). Recovering the precipitate from the mixture is accomplished by allowing the mixture to stand, i.e. no agitation, for about ½ to about 1 hour. The precipitate is removed from the liquid in a conventional manner such as filtration, centrifugation or decantation using conventional equipment for such methods. The recovered precipitate is mainly sugar ester.

Next, the recovered precipitated sugar ester is washed with a volatile organic solvent (See step 14 of FIG. 1). This step is conducted in a conventional manner such as suspending the solid precipitate in the solvent or leaching the solid with the liquid. Good results have been obtained by suspending the solid precipitate in the solvent at ambient temperature and pressure until thorough mixing is accomplished. The volatile organic solvent carries away residual reaction solvents and fatty acyl ester. Preferably the washing step is repeated, twice, so that the recovered precipitate has been washed with the volatile organic solvent a total of three times (See step 18 of FIG. 1). The volatile organic solvent used in the present invention is a liquid at ambient temperature and pressure. The preferred volatile organic solvents are ketone (R-CO-R') having 3 to 6 carbon atoms such as methyl ketone ($CH_3COCH_3$), methyl ethyl ketone ($CH_3COC_2H_5$), and methyl isobutyl ketone ($CH_3COCH_2CH(CH_3)_2$); and ethers (R-O-R') having 4 to 8 carbon atoms such as diethyl ether ($C_2H_5OC_2H_5$), dipropyl ether ($C_3H_7OC_3H_7$), methyl A-propyl ether ($CH_3OC_3H_7$). Methyl ethyl ketone is the preferred organic solvent. Washing is conducted at ambient temperature.

The organic solvent washed precipitate is recovered in a conventional manner such as by centrifugation, filtration or decantation using conventional equipment for such methods.

Preferably, the organic solvent washed sugar ester is then dried in a conventional manner using conventional equipment (See step 20 of FIG. 1). Suitable drying techniques include freeze-drying, spray-drying and drum-drying. Care must be taken during the drying step not to burn or discolor the sugar ester.

Figure 2:
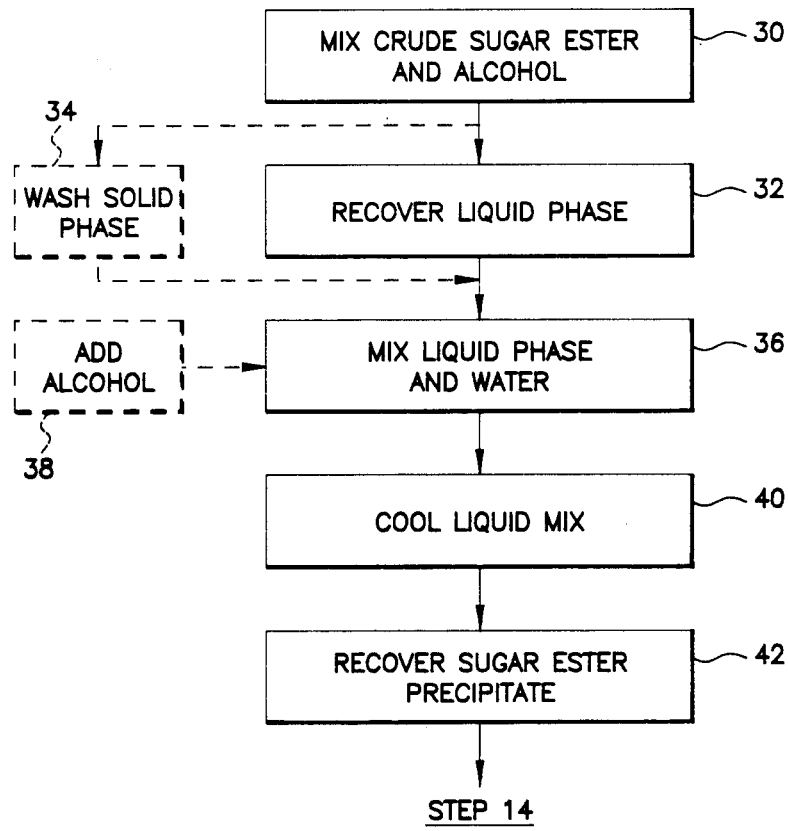
FIG. 2 illustrates a portion of a preferred embodiment of the present invention wherein the crude sugar ester reaction product is obtained from a transesterification process that employs an anhydrous solvent such as the one taught in the '990 patent.

As shown in FIG. 2, when the crude sugar ester reaction product is obtained from a transparent emulsion process such as the one taught in the '333 patent, the step of forming a mixture of crude sugar ester reaction product, water and alcohol, is accomplished in a two step mixing process (See step 10 of FIG 1).

If the crude sugar ester reaction product from a transparent emulsion process such as the one taught in the '333 patent is not in a particulate form, then the reaction mixture is preferably crushed to between about 20 to about 70 mesh size. Crushing is accomplished in a conventional manner.

First, the particulate crude sugar ester reaction product is mixed, with the aliphatic alcohol having from 1 to 4 carbon atoms at a temperature of about 40° C. and above and, more preferably, between about 40° C., to below the boiling point of the alcohol (see step 30 of FIG. 1). Even more preferred, the mixing is conducted at a temperature between about 40° C. to about 60° C. Good results have been obtained at about 50° C. When handling small quantities of crude sugar ester reaction product, the alcohol itself is heated to the appropriate temperature and mixed with the particulate crude sugar ester reaction product, the crude sugar ester reaction product being at ambient temperature. With larger quantities, heat is provided to the components of the mixture by such means as a jacketed vessel or a heating coil thereby allowing the mixing to be conducted at the appropriate temperature. The temperature is that of the components during mixing.

The mixing is accomplished in a conventional manner using conventional equipment, such as a beaker with magnetic stirrer or a vessel equipped with an impeller. The volume of alcohol used in step 30 of the process illustrated in FIG. 2 is between about 1 to about 5 mls per gram of solid crude sugar ester reaction product. The mixing of the alcohol and crude sugar ester reaction product is conducted to obtain thorough mixing of the components and until two phases form, a solid phase which is the undissolved residue from the crude sugar ester reaction product, and a liquid phase. The sugar ester is predominately dissolved in the liquid phase.

After mixing the two components thoroughly, the liquid phase is recovered, (See step 32 of FIG. 2). Such recovery is accomplished in a conventional manner, such as filtration, centrifugation or decantation using conventional equipment for such methods. Preferably, additional warm aliphatic alcohol having 1 to 4 carbon atoms is used to wash, the solid phase which remains after recovery of the liquid phase (See step 34 of FIG. 2). Washing is accomplished in a conventional manner such as by resuspending the solid phase in the wash alcohol or by leaching the solid with the liquid. This wash alcohol is combined with the recovered liquid. The warm alcohol used to wash the solid residue is preferably about 40° C. to below about the boiling point of the alcohol, and preferably about 40° C. to about 50° C. The volume of alcohol used in step 34 of FIG. 2 is preferably about 10% of initial volume of alcohol used in step 30 of FIG. 2.

Next, the recovered liquid phase and any liquid obtained from wash step 34 of FIG. 2 is mixed with water (See step 36 of FIG. 2). The mixing is conducted in a conventional manner using conventional equipment such as a beaker with magnetic stirrer or a vessel equipped with an impeller. The amount of water used is between about 1 to about 5 times the volume of the combined liquid obtained from wash step 34 of FIG. 2 and recovered as a liquid phase in step 32 of FIG. 2. If the water added in 36 causes the volume percent of alcohol to be less than about 50%, then alcohol must be added to the liquid phase to raise the volume percent of alcohol to about 50% (See step 38 of FIG. 2). Mixing is continued to obtain thorough mixing of the components and is conducted at a temperature of about 40° C. and above and L preferably between about 40° C. to below about the boiling point of the alcohol, more preferably, between about 40° C. to about 60° C.

Once thorough mixing of the alcohol, water and crude sugar ester is accomplished, mixing is ceased and the vessel allowed to stand and cool such that a precipitate forms (See step 40 of FIG 2). Some precipitate will start to form when the water is mixed with the liquid phase. Allowing the mixture to cool causes the remaining precipitate to form. The mixture is cooled to below about 30° C. and more preferably to a temperature between about 20° C. to about 30° C. Good results have been obtained at about 25° C.

The precipitate is recovered, in a conventional manner such as filtration, centrifugation or decanting in a conventional manner (See step 42 of FIG. 2). The recovered precipitate is then subjected to the remaining steps, 14–18 of FIG. 1, as described above.

The alcohols used in the mixing step 30, wash step 34 and step 38 of FIG. 1 are aliphatic alcohols having 1 to 4 carbon atoms. Suitable alcohols include methanol, ethanol, propanol, isopropanol, normal butanol, isobutanol and secondary butanol. Preferably, the same alcohol is used in steps 30, 34 and 38.

As a practical matter, both steps 30 and 36 of FIG. 1 are conducted at about 40° C. and above. They need not be conducted at the same temperature and, in fact, it has been found that the water can be added to the warm mix of alcohol and water without the need for additional heat so long as thorough mixing is accomplished between the three components of alcohol, water and crude sugar ester at a temperature of about 40° C. and above. If due to the size and nature of the mixture, the temperature of the components drops below about 40° C. during mixing, then heat can be added to the components in a conventional manner such as conducting the mixing in a jacketed vessel or a heating coil. It will be recognized by those of skill in the art that if the alcohol and crude sugar ester mix is above about 40° C. then adding water at ambient temperature and quickly mixing the three components, alcohol, water and crude sugar ester, to obtain thorough mixing that the temperature during mixing will be about 40° C. and above.

Figure 3:
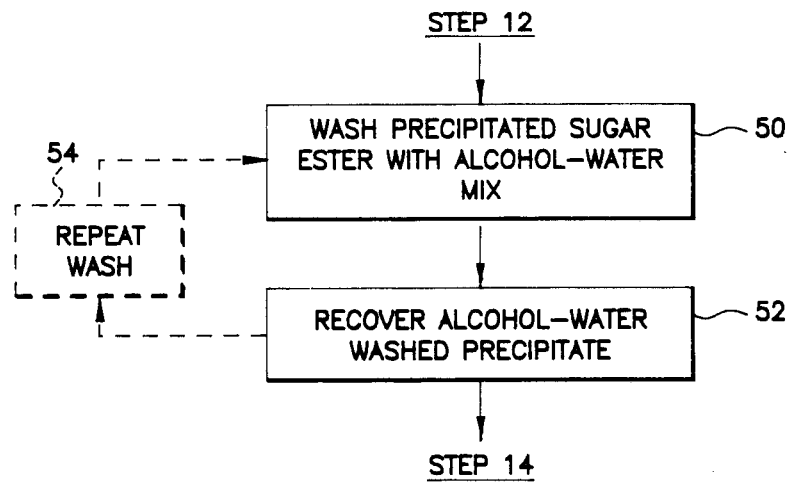
FIG. 3 illustrates a preferred portion of a preferred embodiment of the present invention wherein the crude sugar ester reaction product is obtained from a transparent emulsion process such as the one taught in the '333 patent.

Preferably, when the crude sugar ester reaction product is obtained from a synthesis process that occurs in an anhydrous solvent, such as the one taught in the '990 patent, an intermediate alcohol water wash step is employed. As shown in FIG. 3, the precipitate from step 12 of FIG.. 1 is washed with a mix of alcohol and water. In the washing step 50 of FIG. 3, the precipitate recovered in step 12 of FIG. 1 is washed in a conventional manner such as by suspending the precipitate in the alcohol water mix or by leaching the solid with the liquid mix. Washing step 50 of FIG. 3 is done at ambient temperature.

The alcohol water mix consists of water and an aliphatic alcohol having from about 1 to about 4 carbon atoms. Such alcohols include methanol, ethanol, propanol, isopropanol, normal butanol, isobutanol and secondary butanol. The water is obtained from any conventional source. Substantially equal volumes of the alcohol water mix are mixed with the precipitate. Good results have been obtained with an ethanol water mix. The proportions by volume of alcohol to water are from about 10:90 to about 90:10. Good results have been obtained with a 50:50 mix. Any conventional source of these alcohols may be used. The water and alcohol mix is prepared in a conventional manner. The alcohol used in step 10 of FIG. 1 is suitable for use in step 50 of FIG. 3.

The alcohol water washed precipitate is recovered in a conventional manner such as by decantation, centrifugation and filtration (See step 52 of FIG. 3).

Preferably, washing step 50 of FIG. 3 is repeated. once can be repeated multiple times with loss of product. The remaining steps 14–18 of FIG. 1 are conducted as described above.

Forming the mixture of water, alcohol and crude sugar ester reaction product obtained from the anhydrous solvent process is accomplished using conventional equipment in a conventional manner such as a beaker with a magnetic stirrer or a vessel with an impeller. Good results have been obtained by adding a mixture of water and alcohol to the crude sugar ester reaction product and then thoroughly mixing the water, alcohol and crude sugar ester reaction product. Such mixing is done at ambient temperature and pressure.

Once the water, alcohol and crude sugar ester reaction product are thoroughly mixed, the mixing is ceased and the contents of the vessel are allowed to stand so that a precipitate forms. Good results have been obtained by allowing the contents of the vessel to stand for between about ½ to about 1 hour at ambient temperature and pressure.

The proportions by volume of alcohol to water are from about 10:90 to about 90:10. Good results have been obtained with a 50:50 mix of alcohol and water. A substantially equal volume of the alcohol water mix is mixed with the crude sugar ester reaction product. In other words, volume to volume ratio of the crude sugar ester reaction product to the alcohol water mix is about 1:1. The water and alcohol are premixed in a conventional manner.

The precipitate, which is primarily the sucrose ester, is recovered in a conventional manner such as filtration, centrigutation or decantation. Filtration, centrifugation and decantation are accomplished using conventional equipment. The alcohol water mix used in step 10 of FIG. 1 can be the same alcohol water mix used in step 50 of FIG. 3.

These and other aspects of the present invention may be more fully understood by reference to the following examples.

EXAMPLE 1

This example illustrates separation and purification of a sucrose ester from a transparent emulsion reaction mixture.

Preparation crude sucrose ester reaction product by a transparent emulsion synthesis Example V of the '333 patent was employed to obtain a reaction mixture. The following components were combined initially:
Sucrose 80.4
Water 166.8 ml.
Sucrose monostearate 40.5
Sodium stearate 12.3

The sucrose and emulsifiers were dissolved in the water in a three-neck flask fitted for heating, stirring and vacuum distillation. The contents of the flask were then heated to 80°–85° C., vacuum applied and the water was removed by distillation. The last portion of the water was removed by at 90° C., 4 mm Hg. pressure.

The solution was initially somewhat opalescent in appearance but clarified after about 50 ml. of water was distilled. Frothing occurs and a few drops of silicone antifoam were added. Stirring was also more difficult as the last portion of the water was removed.

After all the water had been removed by vacuum distillation, 75.0 g. of an equal weight mixture of methyl stearate and methyl palmitate and 0.75 g. of anhydrous potassium carbonate were blended with the dry mixture of sucrose and emulsifiers. The mass was then heated with stirring for about 4½ hours, while at 90° C., 3 mm Hg. pressure. Then the temperature was raised to 150° C. for about 45 minutes, 3 mm Hg. pressure. A reaction mixture resulted from this process.

Purification and Separation

About 10 g. of the reaction mixture was crushed and mixed in a beaker with 50 mls. of ethanol and heated to 50° C. for 30 minutes while the contents of the beaker were stirred. A solid and a liquid phase remained after 30 minutes of stirring.

The liquid phase was recovered by filtering the contents of the beaker through a glass wool plug while the contents were still warm (50°–40° C.). An additional 10 mls. of warm (50° C.) ethanol was passed through the glass wool filter to wash the retained solid material.

The filtrate including the wash solvent was immediately mixed with 90 mls. of water. The water was at ambient temperature. The mixture was allowed to cool and come to ambient temperature, about 25° C., whereupon a precipitate formed. This precipitate was recovered by centrifugation at 24,000 xg. at 10° C. for 15 minutes.

The recovered precipitate was then mixed, with 10 mls. of methyl ethyl ketone. The organic solvent washed precipitate was recovered by centrifugation in a manner as described above.

The resulting precipitate was dried in an oven and analyzed by gas chromatography to contain 84% sucrose ester and 16% fatty acid.

EXAMPLE 2

This example illustrates the recovery of a substantially pure sucrose ester from an anhydrous reaction mixture.

Preparation of a crude sucrose ester reaction product from a synthesis is an anhydrous solvent. A mixture comprising 40 grams of sucrose, 140 mls. of anhydrous DMSO, 125 grams of methyl stearate and 1 gram of potassium carbonate was formed. The methyl stearate, potassium carbonate and sucrose had, prior to mixing, been rendered anhydrous by drying them in a vacuum oven. The mixed components were then stirred and heated to a temperature of 90°–95° C. and held under pressure of about 80 to 100 mm Hg. for about 18 hours. Then, the reaction vessel was allowed to cool to room temperature (20° C.). The resulting crude sucrose ester reaction product had a volume of about 200 mls.

Separation and Purification

In a beaker, the crude sucrose ester reaction product was added to 200 mls. of a 50:50 mix of ethanol and water and stirred with a magnetic stirrer. The stirring was ceased once the contents of the vessel were fully mixed and the vessel was allowed to stand for 1 hour at room temperature. A precipitate formed at the bottom of the beaker which was collected by centrifugation at 24,000 xg for 15 minutes.

The collected precipitate was then mixed with 200 mls. of the ethanol/water solution at room temperature to perform an alcohol water wash. The alcohol water washed precipitate was collected by centrifugation as described above. This alcohol water wash step was repeated one time for a total of two alcohol water washes.

The recovered alcohol water washed precipitate was then mixed with 100 mls. of methyl ethyl ketone in a beaker at room temperature to perform the organic solvent wash. The organic solvent washed precipitate was recovered by centrifugation as described above. The organic solvent wash was repeated three times.

The recovered organic solvent washed precipitate was then dried in a vacuum oven. By conventional gas chromatographic techniques, the dried product was found to contain 78% sucrose ester and 22% stearic acid.

It will be understood that the claims are intended to cover all changes and modifications of the preferred embodiments of the invention herein chosen for the purpose of illustration which do not constitute a departure from the spirit and scope of the invention.

What is claimed is:

1. A method for purifying a sugar ester product from a crude reaction mixture containing the sugar ester product, which is produced by a solvent-free, transparent emulsion process, which consists essentially of:
   dissolving the crude reaction mixture in a lower aliphatic alcohol to produce a solution with undissolved residue;
   removing undissolved residue from the solution to produce a clarified solution; and
   combining the clarified solution with a volume of water that is approximately 1 to 5 times the volume of the clarified solution to form a precipitate of the purified sugar ester.

2. A method according to claim 1 wherein the dissolution step is conducted at a temperature of at least 40° C.

3. A method according to claim 1 wherein the lower aliphatic alcohol has from 1 to 4 carbon atoms.

4. A method according to claim 1 which further comprises washing the precipitate of purified sugar ester with a volatile organic solvent.

5. A method according to claim 4 wherein the volatile organic solvent is a ketone of 3 to 6 carbons or an ether of 4 to 8 carbons.

6. A method according to claim 1 wherein the dissolution step is conducted at a temperature of from about 40° C. to about 60° C. and the water is added while said temperature is maintained.

7. A method according to claim 6 wherein the combined mixture of clarified solution and water is cooled to cause precipitation.

8. A method for purifying a sugar ester product from a solvated, crude reaction mixture containing the sugar ester product, which is produced by a solvated transesterification process, which consists essentially of:
combining the solvated, crude reaction mixture with a solvent system of water and a lower aliphatic alcohol wherein the volume of the solvent system is approximately equal to the volume of solvated, crude reaction mixture and the volume to volume proportion of water to alcohol in the system is from about 90:10 to about 10:90, to form a precipitate of the purified sugar ester product.

9. A method according to claim 8 which further comprises recovering and washing the precipitate with a fresh portion of solvent system.

10. A method according to claim 9 further comprising washing the system-washed-precipitate with a volatile organic solvent.

11. A method according to claim 10 wherein the volatile organic solvent is a ketone 3 to 6 carbons or an ether of 4 to 8 carbons.

12. A method according to claim 5 or 10 wherein the volatile organic solvent is selected from the group consisting of methyl ethyl ketone, methyl isobutyl ketone, diethyl ether, dipropyl ether, methyl n-propyl ether and methyl ketone.

13. A method according to claim 8 wherein the lower aliphatic alcohol has from 1 to 4 carbons.

14. A method according to claim 8 wherein the proportion of water to aliphatic alcohol in the solvent system is about 1:1 by volume.

15. A method according to claim 8 wherein the precipitate is formed by allowing the combination of crude reaction mixture and solvent system to stand at ambient temperature until the precipitate forms.

16. A method according to claim 1 or 8 wherein the aliphatic alcohol is selected from the group consisting of methanol, ethanol, propanol, isopropanol, normal butanol, isobutanol and secondary butanol.

* * * * *

UNITED STATES PATENT AND TRADEMARK OFFICE
CERTIFICATE OF CORRECTION

PATENT NO. : 4,983,731

DATED : January 8, 1991

INVENTOR(S) : Wagner et al.

It is certified that error appears in the above-identified patent and that said Letters Patent is hereby corrected as shown below:

Column 1, line 39, before "hereinafter" insert --(--;

Column 1, line 40, after "'333" insert --patent)--;

Column 5, line 26, for "36" read --step 36 of Fig. 2--;

Column 5, line 32, after "above and" delete --L--.

Column 5, line 51, for "Fig. 1" read --Fig. 2--;

Column 5, line 56, for "Fig. 1" read --Fig. 2--;

Column 6, line 38, after "once" insert --, but--; and

Column 10, line 10, after "ketone" insert --of--.

Signed and Sealed this

Twenty-second Day of September, 1992

Attest:

DOUGLAS B. COMER

*Attesting Officer*   *Acting Commissioner of Patents and Trademarks*